United States Patent
Scholtens et al.

(10) Patent No.: US 8,569,077 B2
(45) Date of Patent: *Oct. 29, 2013

(54) IMAGING OF IMMUNOMAGNETICALLY ENRICHED RARE CELLS

(75) Inventors: Tyco M. Scholtens, Enschede (NL); Frederik Schreuder, Enschede (NL); Jan Greve, Oldenzaal (NL); Arjan G. J. Tibbe, Deventer (NL); Leon W. M. M. Terstappen, Amsterdam (NL)

(73) Assignee: Veridex, LLC, Raritan, NJ (US)

( * ) Notice: Subject to any disclaimer, the term of this patent is extended or adjusted under 35 U.S.C. 154(b) by 825 days.

This patent is subject to a terminal disclaimer.

(21) Appl. No.: 12/467,932

(22) Filed: May 18, 2009

(65) Prior Publication Data
US 2009/0286264 A1    Nov. 19, 2009

Related U.S. Application Data

(60) Provisional application No. 61/054,219, filed on May 19, 2008.

(51) Int. Cl.
*G01N 33/553* (2006.01)

(52) U.S. Cl.
USPC ............................................. 436/526

(58) Field of Classification Search
USPC .......................................... 436/526
See application file for complete search history.

(56) References Cited

U.S. PATENT DOCUMENTS

| | | | |
|---|---|---|---|
| 5,985,153 A | 11/1999 | Dolan et al. | |
| 6,136,182 A * | 10/2000 | Dolan et al. | 210/94 |
| 6,249,341 B1 * | 6/2001 | Basiji et al. | 356/73 |
| 6,790,366 B2 | 9/2004 | Terstappen et al. | |
| 6,890,426 B2 | 5/2005 | Terstappen et al. | |
| 2006/0147901 A1 * | 7/2006 | Jan et al. | 435/4 |
| 2006/0257847 A1 | 11/2006 | Scholtens et al. | |

FOREIGN PATENT DOCUMENTS

| | | |
|---|---|---|
| JP | 02-118451 | 5/1990 |
| WO | WO 2005/027037 A2 | 3/2005 |
| WO | WO2009143149 | 11/2009 |

OTHER PUBLICATIONS

Tibbe, A., et al. Optical Tracking and Detection of Immunomagnetically Selected and Aligned Cells, Nature Biotechnology, vol. 17, pp. 1210-1213 (1999).

European Search Report dated Oct. 6, 2011 for corresponding Patent Application No. EP09751377.

* cited by examiner

*Primary Examiner* — Mark Shibuya
*Assistant Examiner* — Pensee Do

(57) ABSTRACT

A method for removing excess unbound ferrofluid and imaging immunomagnetically enriched circulating tumor cells is provided. A vessels having a preformed grooves in the viewing surface is optimally designed for cell alignment and imaging. After separating the unbound particles by centrifugation, an externally-applied force is applied to transport magnetically responsive particle-CTC complex toward the transparent collection wall. The grooved inner surface of the viewing face of the chamber provide uniform distribution of the particles for easy imaging. The invention is also useful in conducting quantitative analysis and sample preparation in conjunction with automated cell enumeration techniques as in quantitative analysis of CTC in disease.

7 Claims, 3 Drawing Sheets

# IMAGING OF IMMUNOMAGNETICALLY ENRICHED RARE CELLS

CROSS-REFERENCE TO RELATED APPLICATIONS

This application claims priority to and the benefit of U.S. provisional patent application Ser. No. 61/054,219, filed May 19, 2008, which application is incorporated herein by reference in its entirety.

BACKGROUND

The present invention relates to improved apparatus and methods for performing qualitative and quantitative analysis of microscopic biological specimens. In particular, the invention relates to such apparatus and methods for isolating, collecting, immobilizing, and/or analyzing microscopic biological specimens or substances which are susceptible to immunospecific or non-specific binding with magnetic-responsive particles having a binding agent for producing magnetically-labeled species within a fluid medium. As used herein, terms such as "magnetically-labeled specimen" shall refer to such biological specimens or substances of investigational interest which are susceptible to such magnetic labeling.

U.S. Pat. No. 5,985,153 describes an apparatus and method wherein an external magnetic gradient is employed to attract magnetically labeled target specimens present in a collection chamber to one of its surfaces, and where an internal magnetic gradient is employed to obtain precise alignment of those specimens on that surface. The movement of magnetically labeled biological specimens to the collection surface is obtained by applying a vertical magnetic gradient to move the magnetically labeled biological specimens to the collection surface. The collection surface is provided with a ferromagnetic capture structure, such as plurality of ferromagnetic lines supported on an optically transparent (viewing) face of a sample chamber.

Once the magnetically labeled biological specimens are pulled sufficiently close to the surface by the externally applied gradient, they come under the influence of an intense local gradient produced by the ferromagnetic collection structure and are immobilized at positions laterally adjacent thereto. The local gradient preferably exceeds adhesion forces which can hold the biological specimens to the transparent surface after they collide with the surface. Alternatively, the adhesiveness of the surface must be sufficiently weak to allow the horizontal magnetic force to move the magnetically labeled biological specimens towards the ferromagnetic structures. The smoothness and the hydrophobic or hydrophilic nature of the surface are factors that can influence the material chosen for the collection surface or the treatment of this surface to obtain a slippery surface.

U.S. Ser. No. 10/733,829 and U.S. Pat. No. 6,790,366 describe methods and apparatus for separating, immobilizing, and quantifying biological substances in a fluid sample, incorporating the principles of the externally applied gradient described above, and further incorporate a high internal gradient magnetic capture structure on the transparent collection wall. The capture structure encourages a uniform alignment of captured biological substances for quantitative analysis with automated enumeration techniques.

U.S. Ser. No. 11/447,562 describe small V-shaped grooves on the fluid side of the optically transparent (viewing) face of the chamber to align the target specimens for automated optical analysis. The small V-shaped grooves on the fluid side of the optically transparent (viewing) face of the chamber, and with the optimum dilution of magnetically-labeled specimens provides an alignment surface for automated optical analysis. Magnetically-labeled specimens and unbound magnetic particles move toward the inner surface of the chamber's viewing face, under the influence of the externally applied magnetic gradient. When they approach the surface, they come in contact with the slope of the V-shaped groove, forcing the magnetically-labeled specimens and unbound magnetic particles to move to the top of the groove.

U.S. Ser. No. 11/344,757 describe a device and method for automated collection and image anlaysis of detectably labeled rare target cells. These magnetically labeled rare cells are subjected to Time Delay Integration Imaging (TDI) in the CellTracks Platform. However when assessing circulating tumor cells (CTC) in the blood of cancer patients in order to correlate with disease activity, unbound magnetic particles that are left over from immunomagnetic separation will distort the image and interfere with confirmation of a captured target as a CTC.

The present invention provides a small groove design that allows for complete removal of the unbound magnetic particles in the analysis of labeled rare cells using TDI in the CellTracks platform.

DETAILED DESCRIPTIONS

Circulating tumor cells (CTC) in blood of cancer patients are known to correlate with disease activity. The CellTracks platform provides a magnetic enrichment and image analysis of suspect target cells for enumeration and correlation with disease state. Targets such as cells, cell debris, and cell components are collected against a collection surface of a vessel without subsequent alignment adjacent to a ferromagnetic collection structure. These cells include white blood cells, cells of epithelial origin, endothelial cells, fungal cells, and bacterial cells. The collection surface is oriented perpendicular to a magnetic field gradient produced by external magnets. The resultant image includes magnetic nanoparticles and magnetically labeled biological specimens, collected in a substantially homogeneous distribution on the optically transparent face of the chamber while non-selected entities remain below in the fluid medium.

The incorporation of Time Delay Integration (U.S. Ser. No. 11/344,757) into the CellTracks platform in rare cell analysis is used to rapidly detect and characterize CTC. Immunomagnetic separation of target rare cells (CTC) is accomplished by EpCAM positive selection. Circulating cells expressing the antigen for the epithelial cell adhesion molecule (EpCAM) are selected by the monoclonal antibody specific or EpCAM and covalently linked to magnetic nanoparticles. The complex is separated from the remaining blood constituents when exposed to a magnetic field.

Subsequent analysis of the captured target is determined through a series of fluorescent labeling of components within the cell. The fluorescent dye DAPI is used to label the nuclei of CTC and non-specifically selected leukocytes, the cytoskeleton of CTC is labeled with Cytokeratine-PE and the leukocytes with CD45-APC. The labeled cells are magnetically manipulated to align along an analysis surface. However in this system, unbound magnetic particles that are left over from immunomagnetic separation will cause image distortion and reduce the ability to confirm the presence of a CTC.

To provide for spatially patterned collection of target specimens for qualitative and quantitative analysis of microscopic biologic samples, the present invention relates to making and using pre-molded structures on the inner surface of the imaging chamber. Generally, pre-molded grooves are long v-shaped grooves, pre-molded into the inner portion of the viewing surface on the imaging chamber. These structures provide an alignment of cells as good as or even better than previously reported Ni lines. Furthermore, they are made from a highly transparent material, optically suited for imaging the entire cell.

Figure 1:
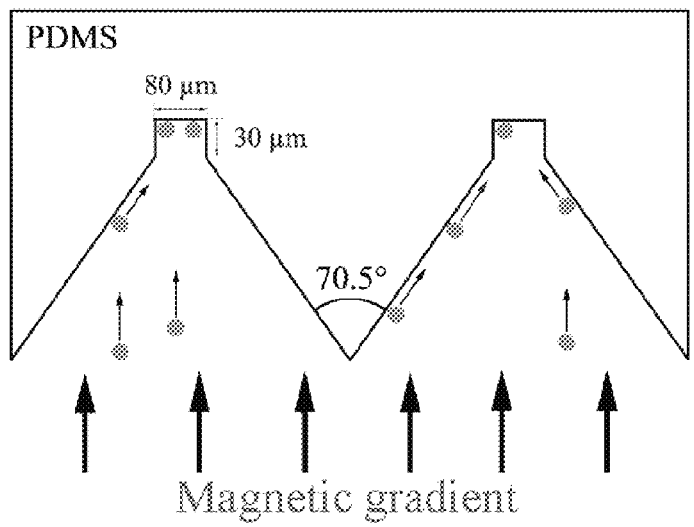
FIG. 1 is a schematic diagram of the cell alignment structure.

FIG. 1 illustrates the principle of cell alignment using the grooves of the present invention. Magnetically induced cell movement within the chamber occurs in the present of a magnetic gradient. Here, the magnetically labeled cells will either collide with the inclined surface of the structure (alignment surface) and slide into the top of the groove (indicated imaging surface), or they will directly hit the top of the imaging surface. In either situation, the cells will align in the groove, allowing for subsequent imaging.

In order for sufficient movement along the inclined surface of the groove, the surface should be flat and cells prohibited from sticking to the walls. To achieve a smooth precise design, known wafer etching technologies are used. However because of expense and optical requirements, silicon wafers are not appropriate, rather polydimethylsiloxane (PDMS) replica molding provides a composition that will meet these requirements. Compositions that will meet this criteria are also considered in the present invention. Structures, etched onto a silicon wafer, are the inverse of the eventual design, and provide the PDMS mold with the correct shape when poured onto the silicon mold. After curing, this shape is cut into dimensions that would allow replacement of the glass surface of the imaging chamber.

Etching can be accomplished on any optically transparent material that can be used in the manufacture of the chamber. By example, silicon wafers can be used in etching because of the ease of precision, fine detail, and easily reproducible. Any material with similar characteristics and known in the art is considered in the present invention. Etching of the structure uses two common etching techniques. First an etch mask that is needed to etch the grooves is created. This mask is created using BHF (Buffered Hydrofluoric acid) etching. Once BHF etching is complete, thin layers of $SiO_2$ are left on the silicon wafer at places where no groove should be etched. Anisotropic etching is also used to etch the grooves. Here, KOH is used as etchant. When this process is applied to a properly orientated wafer, V-grooves are etched, limited by the crystal plane of the silicon wafer. Accordingly, a highly reproducible and constant etch angle is produced. The angle depends on the wafer orientation with one embodiment as shown in FIG. 1 at 70.5 degrees. An other technique is Deep Reactive Ion Etching (DRIE). By using this technique it is possible to etch structures with a high aspect ratio (ratio between length and width of the structure). DRIE cyclically alternates between etch and deposition steps forming scalloped sidewalls.

PDMS molding is used to obtain a positive imprint on the fabricated wafer. PDMS or Polydimethylsiloxane (Dow Corning (Sylgard 184, Dow Corning, Midland, Mich., USA) is a polymer containing the siloxane bond between Si (Silicon) and O (Oxygen). The polymers molecules are linked together to form longer polymers with an average number around 50 to 100.

The final PDMS is obtained with the addition of a cross-linker. The cross-linker connects with the polymers to form long networks of polymers, resulting in a clear, elastic, chemically inert, thermally stable material. After polymerization, the PDMS forms a clear flexible substance which adheres to very few materials and is not hygroscopic, thus preventing any sticking of cells to the sides due to the fact that PDMS adheres to very few materials. Furthermore, it is thermally stable and transparent from approximately 300 to 900 nm. These characteristics are all important for its use in a fluorescent imaging system and the transmission of visible light. After formation, the grooves are cut into the dimensions of the viewing face of the chamber.

In order to remove most of the excess magnetic particle with minimal cell loss, the cell alignment structure shown in FIG. 1 was developed for the viewing surface. FIG. 1 provides an overview of the cell alignment structure. A PDMS microstructure shown in FIG. 1 was developed to align the cells in predetermined areas and reduce imaging time. The design consists of a PDMS chip of 30×2.7 $mm^2$ containing 6 channels that are 80 um wide and 30 mm long. These PDMS chips are imprinted from a wafer mold. We chose PDMS because of its excellent transmission properties, replicating capabilities and ease of use. This configuration reduces the imaging time for a sample from 32 to 12 minutes.

Figure 2:
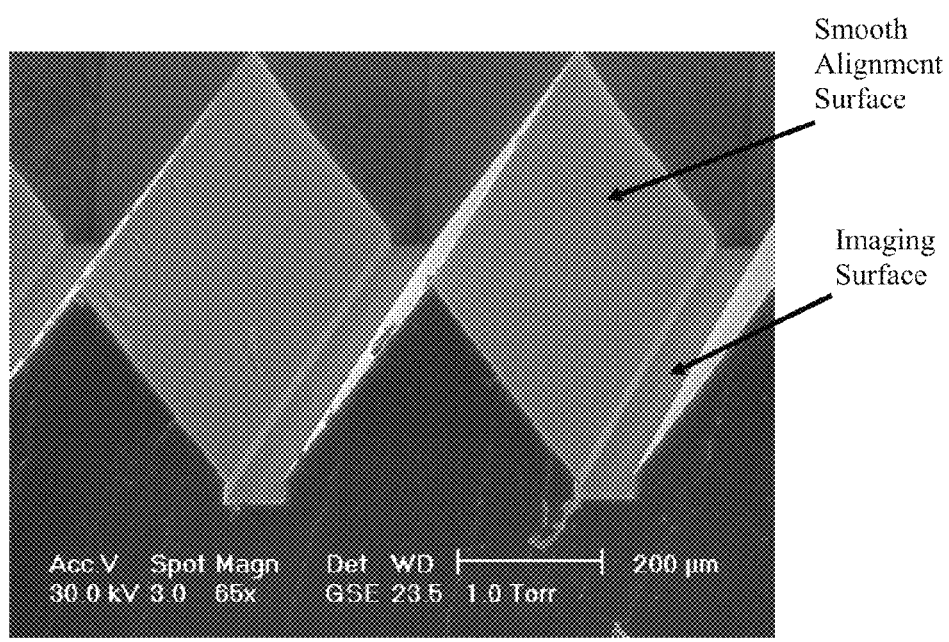
FIG. 2 shows a picture of the PDMS imprint using a scanning electron microscope with the smooth alignment and imaging surfaces.

FIG. 2 shows a scanning electron micrograph of a PDMS imprint having the structure used in the present invention. The picture shows the smooth alignment and imaging surfaces on the viewing surface.

Figure 3:
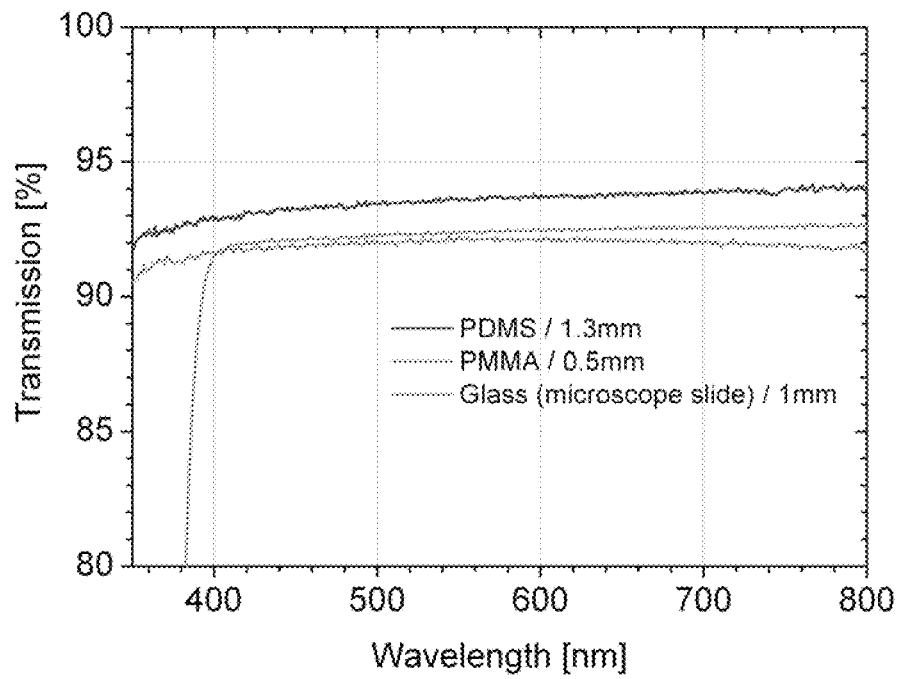
FIG. 3 shows the transmission spectrum of a PDMS slab at 1.3 mm and a PMMA slab at 0.5 mm thickness compared with a typical glass microscope slide of 1.0 mm thick.

FIG. 3 compares the transmission spectrum of the thickness of the PDMS used in the present invention with a typical glass microscope slide. With a thickness of 0.5 mm, PMMA tracks the transmission of a glass microscope slide between 400 nm and 800 nm wavelengths.

Figure 4:
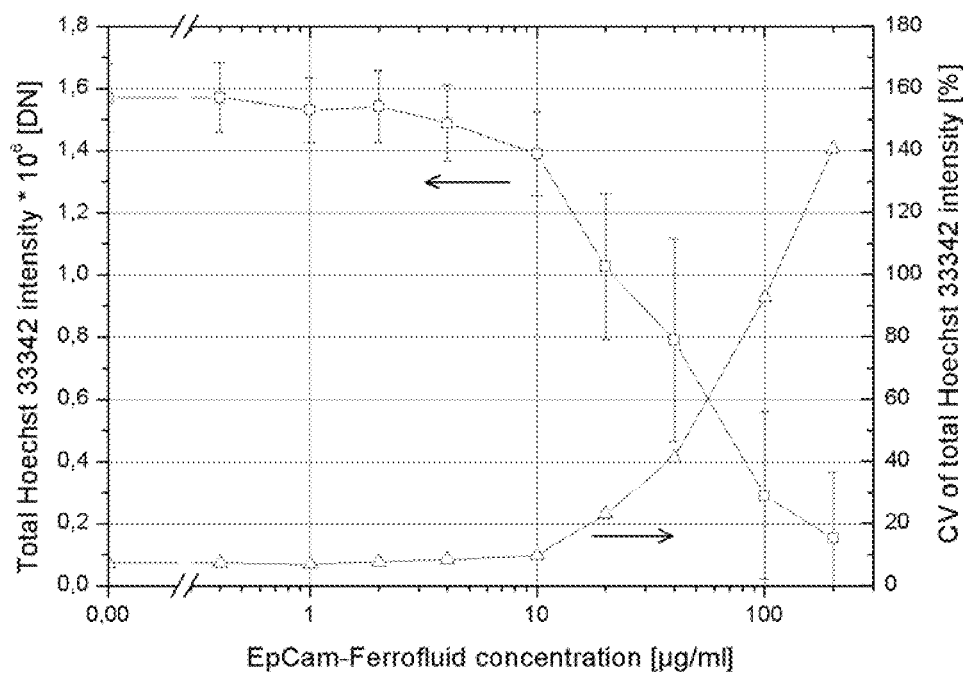
FIG. 4 shows the effect of excess unbound magnetic particles on the intensity of the image. Increasing levels of EpCAM ferrofluid results in a decrease in image intensity and an increase in variation in assessing intensity.

Excess of conjugated magnetic particles (EpCAM-ferrofluid) are used to ensure maximum CTC recovery. However, during imaging the excess ferrofluid forms elongated aggregates on the imaging surface, which influences quantitative and qualitative imaging of the cells. FIG. 4 shows the effect of excess unbound magnetic particles on imaging. The total nuclear intensity drops sharply for concentrations of ferrofluid higher than 2 ug/ml (circles), while the CV rises to 40% for concentrations that are normally found in patient samples, such as 40 ug/ml (triangles).

Figure 5:
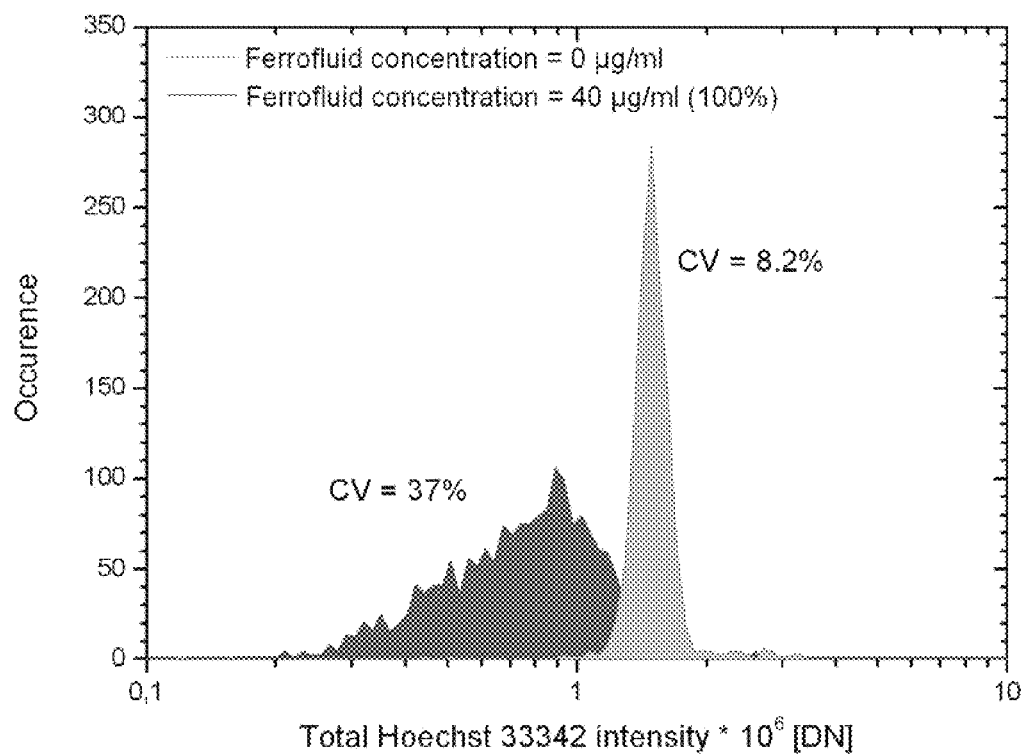
FIG. 5 shows the difference in total intensities when with and without 40 ug/ml ferrofluid present. The distribution is worse with ferrfluid present.

The effect of excess ferrofluid on imaging and the results of the removal method are shown in FIG. 5. SKBR-3 cells imaged with 40 ug/ml ferrofluid concentrations and with 0 ug/ml ferrofluid. The distribution of total intensities is significantly worse for the sample with excess ferrofluid.

Figure 6:
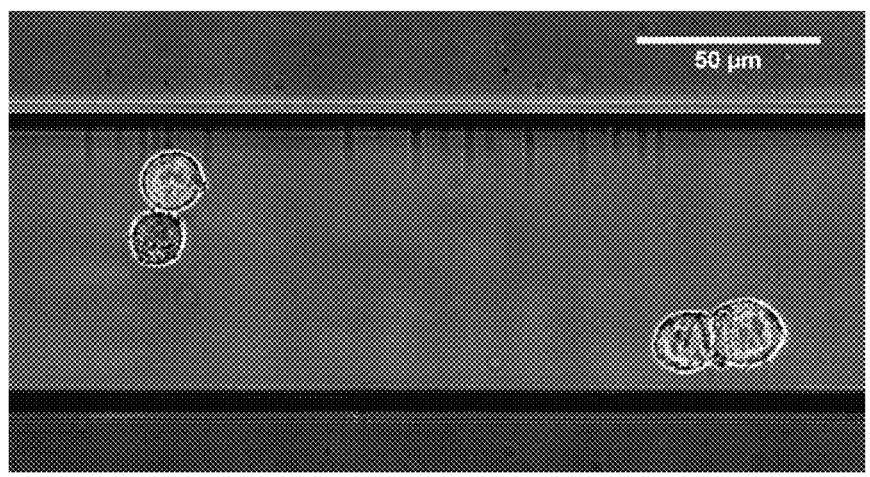
FIG. 6 shows the combined Bright field, DAPI and PE image showing aligned SKBR3 cells.

The present invention avoids this issue and provides a method that spins the sample inside a conical tube at 900 rpm. This forces all the cells in the tube outwards. The ferrofluid particles are much smaller (~175 nm in diameter) and remain randomly distributed in the sample. After several minutes, 60% of the sample is automatically aspirated from the bottom of the rotating tube. This process is repeated 5 times and the SKBR-3 cells aligned along the viewing surface using the PDMS structure in the present invention. FIG. 6 shows the combined bright field, DAPI and PE image of captured SKBR-3 cells aligned along the viewing surface.

Using the method of the present invention, 95% to 97% of excess ferrofluid can be removed, brining the final concentration in a patient sample down to less than 2 ug/ml. This removes enough excess ferrofluid to make optimal quantitative measurements and considerable improvements in the quality of images. Also, the recovery of CTC's ranted between 95% and 99%. Accordingly, ferrofluid removal, using the methods of the present invention, provides for sufficient removal of excess ferrofluid for optimal quantitative measurements. The quality of the images are improved and bright field imaging is possible to obtain additional morphological data on individual CTC's.

While certain of the preferred embodiments of the present invention have been described and specifically exemplified above, it is not intended that the invention be limited to such embodiments. Various modification may be made thereto without departing from the spirit of the present invention, the full scope of the improvements are delineated in the following claims.

The invention claimed is:

1. An improved method for optically analyzing rare cells suspended in a fluid medium, which method comprises:
   a. obtaining a blood sample from a patient suspected of having cancer;
   b. mixing said blood sample with ferrofluid particles linked to an antibody specific for the epithelial cell adhesion molecule_antigen on the surface of epithelial cells;
   c. removing unbound ferrofluid from bound ferrofluid; and
   d. viewing magnetically responsive constituents in the blood sample using Time Delay Integration in a viewing chamber wherein said constituents are uniformly-distributed within a preformed alignment structure containing grooves having an image viewing surface and an alignment surface on the inner surface of the optically-transparent face of said chamber.

2. The method of claim 1 wherein said alignment structures are foxhole-shaped grooves.

3. The method of claim 1 wherein said image viewing surface is 80 um.

4. The method of claim 1 wherein said removing unbound ferrofluid comprises:
   a. spinning said blood sample with ferrofluid particles in a conical tube at 900 rpm;
   b. aspirating the sample from the bottom of said conical tube; and
   c. repeat steps (a) and (b) 5 times.

5. The method of claim 1 wherein said viewing further includes confirming the bound epithelial cell as a circulating tumor cells.

6. The method of claim 5 wherein said confirming comprises:
   a. positive first labeling of the nucleus with 4',6-diamidino-2-phenylindole;
   b. positive second labeling of the cytoskeleton with Cytokeratine phycoerythrin; and
   c. positive third labeling of leukocytes with CD45 allophycocyanin.

7. The method of claim 6 further including bright field examining of captured circulating tumor cells.

* * * * *